United States Patent [19]

Costin

[11] 4,076,622
[45] Feb. 28, 1978

[54] MICROBIOCIDAL MACRORETICULAR ION EXCHANGE RESINS, THEIR METHOD OF PREPARATION AND USE

[75] Inventor: C. Richard Costin, Jenkintown, Pa.

[73] Assignee: Rohm and Haas Company, Philadelphia, Pa.

[21] Appl. No.: 698,626

[22] Filed: Jun. 22, 1976

[51] Int. Cl.$^2$ ............................................. C02B 3/10
[52] U.S. Cl. .................................... 210/64; 210/29; 210/501; 424/79; 424/132
[58] Field of Search .................. 21/58; 210/29, 37 R, 210/38 R, 62, 64, 501; 424/79, 132, 150

[56] References Cited

U.S. PATENT DOCUMENTS

| | | | |
|---|---|---|---|
| 2,396,515 | 3/1946 | Kreidl et al. | 424/132 |
| 2,434,190 | 1/1948 | Barnes et al. | 210/29 |
| 2,692,855 | 10/1954 | Juda | 210/29 |
| 3,454,493 | 7/1969 | Kun et al. | 210/37 R |
| 3,462,363 | 8/1969 | Mills | 210/62 |
| 3,817,860 | 6/1974 | Lambert et al. | 210/29 |
| 3,923,665 | 12/1975 | Lambert et al. | 424/79 |

OTHER PUBLICATIONS

Kunin et al., "A Progress Report on the Removal of Colloids from Water by Macroreticular Ion Exchange Resins", paper presented at the International Water Conference, Pittsburgh, PA, Oct., 1969.

Saunders et al., "Preparation of Biologically Pure Water by Ion Exchange", presented at the Ion Exchange in the Process Industry Conference, London Society of Chemical Industries, London, July 16–18, 1968.

*Primary Examiner*—Charles N. Hart
*Assistant Examiner*—Ivars Cintins
*Attorney, Agent, or Firm*—George W. F. Simmons; William E. Lambert, III

[57] ABSTRACT

This invention relates to large pore macroreticular ion exchange resins which contain chemically or physically bound microbiocides or combinations thereof. This invention also relates to methods of preparation of these microbiocidal compositions and their use in purifying aqueous solutions which are microbially contaminated.

9 Claims, No Drawings

MICROBIOCIDAL MACRORETICULAR ION EXCHANGE RESINS, THEIR METHOD OF PREPARATION AND USE

SUMMARY OF THE INVENTION

This invention relates to large pore macroreticular ion exchange resin compositions which contain a physically bound microbiocide. This invention also relates to the process for preparing these compositions and their methods of use.

BACKGROUND OF THE INVENTION

The problem of microbial contamination of water systems has become a major concern particularly in rural areas. The vast distribution network needed to service areas of low population density, as well as the high cost for the construction of large water treatment plants, makes these methods for resolving the problem both economically and structurally infeasible. In rural areas the microbial contamination of well water, from cess-pools and animal fecal contamination, represent a serious problem.

Another area wherein microbial contamination is a problem is in residential swimming pools. The control systems utilized in these applications usually involves the use of microbiocide release agents at very high concentrations. The major concern in this area of application is the inadequacy of control over the use of such microbiocides and the resultant problems associated with their misuse.

Various methods are known which attempt to provide a solution to the problem of purifying microbially contaminated water. The major approach to the problem has been to provide a means by which controlled amounts of a microbiocide are added to the water system. However, the microbiocide concentration needed in such systems must be sufficiently high to effect rapid microbial kill but must also be low enough to be safe for human consumption. Such microbiocidal systems usually require holding tanks, to increase the residence time, in order to achieve sufficient microbial kill at physiologically safe levels of microbiocide release.

The concept of using silver impregnated carbon systems for water purification is also known. These systems function via sustained release of the silver into the contaminated water. Since high concentrations of silver are needed to rapidly kill the bacteria, a scavenger system must be utilized which will lower the silver concentration to physiologically safe levels. Alternatively, if lower silver concentrations are released into the contaminated water then holding tanks must be utilized to produce a high enough percentage kill of the bacteria to be physiologically acceptable.

It is also known that anion exchange resins can be utilized to separate various bacteria. This work has been reported by S. Daniels and L. Kempe in *Chemical Engineering Progress Symposium Series* vol. 62(69) pp 142-8 (1966).

The Japanese patent 74 80,241 granted Aug. 2, 1974 to Y. Fujiwara and O. Yagi describes the use of strong acid cation exchange resins, impregnated with bactericidal quaternary ammonium cations, for removing bacteria from contaminated water.

The U.S. Pat. Nos. 3,923,665 granted Dec. 2, 1975 and 3,817,860 granted June 18, 1974 both to J. Lambert and L. Fina, and 3,462,363 granted Aug. 19, 1969 to J. Mills disclose the polyhalide form of strong base resins having gel structures and their use in the purification of bacterially contaminated water. J. Woodward and M. Korczynski reported in *Developments in Industrial Microbiology* vol. 14 pp. 361-369 (1973) that these resins tended to leach iodine during use and that an additional activated charcoal bed was needed to obtain no iodine residuals.

DESCRIPTION OF THE PREFERRED EMBODIMENT OF THE INVENTION

The present novel invention relates to large pore macroreticular anion exchange resins containing a chemically or physically bound biocide or combinations thereof and their method of preparation and use as microbiocidal compositions. These macroreticular compositions trap and also kill the microbes in contaminated water, whereas the smaller macroreticular resins or the gel resins do not trap these microbes.

The anion exchange macroreticular resins used in this invention possess large pores which contain a chemically or physically bound microbiocide. The average critical dimension of these pores is such that it can accommodate a microbe such as a bacterial cell which is approximately 10,000A, or viruses which range in size from about 150A to about 2,000A and the like. However, this average critical dimension should not be so large that the resin becomes fragile and cannot withstand mechanical manipulation. The term "average critical dimension" as utilized in the specification and claims is meant to define an average of the narrowest cross-sectional distance of the resin pores.

Thus, the preferred range of average critical dimensions of the macroreticular anion exchange resin pores of this invention is between about 8,000A, and about 500,000A, more preferably between about 10,000A and about 400,000A most preferably between about 25,000A and about 250,000A. Macroreticular anion exchange resins which fall within the above ranges of average critical dimensions of resin pores are commercially available materials. The preferred macroreticular anion exchange resins which can be utilized in this invention are those disclosed in U.S. Pat. No. 3,454,493 granted July 8, 1969 to K. Kun and R. Kunin. The method of preparation of these resins is described in this patent and is incorporated herein by reference.

Other macroreticular resins such as those described in U.S. Pat. Nos. 3,531,463, 3,663,467 and 3,816,355 granted Sept. 29, 1970, May 16, 1972, and June 11, 1974 respectively an also be utilized in this invention and are also incorporated herein by reference.

Here again the average critical dimension of the resin pore must be large enough to accommodate a microbe and yet not so large that the resin becomes fragile.

Both weak and strong base anion exchange resins can be utilized in this invention, however, strong base anion exchange resins are preferred. Among the preferred strong base anion exchange moieties that can be utilized in this invention are quaternary ammonium, tertiary sulfonium, quaternary phosphonium, alkyl pyridinium and the like. The more preferred strong base anion exchange moiety is quaternary ammonium, the most preferred being tertiary methylammonium or dimethylethanol ammonium.

A preferred embodiment of this invention is the microbiocidal compositions wherein the strong base anion exchange macroreticular resins contain a chemically bound microbiocide as exemplified by the polyhalide microbiocides.

Another preferred embodiment of this invention is the microbiocidal compositions wherein the strong base anion exchange macroreticular resins contain physically bound microbiocides as exemplified by heavy metal salts of limited water solubility.

The more preferred embodiment of this invention is the microbiocidal compositions wherein the strong base anion exchange macroreticular resins contain physically bound silver chloride.

The macroreticular microbiocidal compositions of the present invention are capable of purifying microbially contaminated aqueous streams at flow rates of up to about 52 gallons per minute per square foot on a linear flow rate basis; but are preferably utilized at flow rates of up to about 26 gallons per minute per square foot; and are most preferably utilized at flow rates of about 12 gallons per minute per square foot.

On a cubic foot basis, the macroreticular microbiocidal compositions of the present invention are capable of purifying microbially contaminated aqueous streams at flow rates of up to about 20 gallons per minute per cubic foot; but are preferably utilized at flow rates of up to about 10 gallons per minute per cubic foot; most preferably at about 5 gallons per minute per cubic foot.

The term "microbe" and terms derivatized therefrom such as "microbially", "microbiocide" and "microbiocidal" as used in the specification and claims is meant to include such microorganisms as bacteria, viruses, fungi, algae, lichens, molds, slimes and the like; more preferably bacteria, viruses; most preferably bacteria.

The macroreticular microbiocidal compositions of the present invention in addition to their microbiocidal properties discussed above, possess the ability to remove nitrates from contaminated effluents. This is another important advantage especially for application in rural areas where agricultural run-off and its accompanying high concentrations of nitrate fertilizers is an additional problem.

The macroreticular anion exchange resins which are utilized in this invention can be prepared by well-known methods for example see U.S. Pat. Nos. 3,454,493, 3,531,463, 3,663,467 and 3,816,355 disclosed above.

The microbiocidal compositions of this invention can be prepared by the following procedure. The macroreticular anion exchange resin is first preconditioned to be in a suitable anion form. An aqueous mixture of this preconditioned resin is stirred at about 0° C to about 100° C, most preferably at about room temperature, and a suitable water soluble microbiocide is then added to the mixture. The mechanical stirrer is kept at a rate of speed such that mechanical breakage of the resin is kept at a minimum. The mixture is then stirred at about room temperature and is then filtered and washed with water. The resin may be optionally dried at temperatures from about 25° C to about 110° C but is preferably stored in the wet state.

The following reaction sequence is envisioned when the above procedure is utilized in the preparation of the microbiocidal compositions wherein the microbiocide is chemically bound to the large pore macroreticular anion exchange resin. The large pore macroreticular anion exchange resin is preconditioned so as to be in a form suitable for chemical bonding. The term "suitable for chemical bonding" as utilized in the specifications and claims is meant to define an anion form of the resin such that the resulting salt formed by the reaction of the cation associated with the microbiocide and the anion which is exchanged for the microbiocide is water soluble. Thus, the polyhalide anion, which is in a water soluble form, forms a chemical bond with the anion exchange moiety of the macroreticular resin; and replaces the anion which was originally associated with said resin. The cation, originally associated with the polyhalide anion, becomes associated with the anion originally attached to the anion exchange moiety of the macroreticular anion exchange resin, and remains in the aqueous phase.

For the microbiocidal compositions wherein the microbiocide is physically attached to the resin, the following reaction sequence is envisioned. The large pore macroreticular anion exchange resin is preconditioned so as to be in a form suitable for physical bonding. The term "suitable for physical bonding," as utilized in the specification and claims, is meant to define an anion form of the resin such that the anion associated with the resin produces a water insoluble heavy metal salt when it exchanges with the anion of the water soluble heavy metal salt. Thus, the heavy metal cation, which is in a water soluble form, reacts with the anion associated with the anion exchange moiety of the macroreticular resin, and forms a precipitate which becomes physically bound in the pores and on the surfaces of the resin. Water soluble silver salts which can be utilized in this procedure include silver sulfate, silver nitrate, silver acetate, silver carbonate, silver tartarate, silver oxide and the like, preferably silver sulfate.

The following is an alternate procedure which can be utilized in the preparation of the physically bound microbiocidal compositions of the present invention. A mixture of a large pore macroreticular resin which may or may not contain functional groups is mechanically stirred and heated at a temperature from about 25° C to about 110° C in a saturated solution of a sparingly soluble heavy metal salt. The mixture is then cooled to precipitate out the heavy metal salt in the pores and on the surfaces of the resin. The composition is then filtered and washed with cold water. The composition can be optionally dried as above, but is preferably maintained in the wet state.

The following examples are provided to illustrate the preparation and use of the microbiocidal compositions of the present invention and are not to be considered in any way to be limitations of the breadth and scope thereof.

EXAMPLE 1

Preparation of AMBERLITE ® IRA-938(Cl) - Silver Chloride Composition

A. Preconditioning Procedure

Standard procedures used to precondition ion exchange resins intended for food processing uses are followed. The general procedure is to treat AMBERLITE ® IRA-938(Cl), a large pore macroreticular anion exchange styrene/divinyl benzene resin of Rohm and Haas Company, with a 4% sodium hydroxide solution till all the chloride ion has been removed. The macroreticular anion exchange resin is then thoroughly rinsed with water and finally treated with a 4% hydrochloric acid or sodium chloride solution. This cycling process is repeated two additional times; the last cycle being with hydrochloric acid followed by a water rinse.

B. Isopropanol Wash

The final step of the preconditioning procedure is an isopropanol wash to remove trace organics from the resin. The isopropanol wash could be carried out before or after the base-acid cycles. In the procedure where the isopropanol wash is after the acid-base cycles a final wash with water is required.

Preparation of AMBERLITE IRA-938(Cl) Resin - Silver Chloride Microbiocidal Composition The 4000 ml (2,395g) of AMBERLITE IRA-938(Cl) resin preconditioned according to steps (a) and (b) and 2000 ml of deionized water are added to a 12-liter flask equipped with an overhead stirrer. The stirring rate is adjusted to achieve thorough mixing without causing excessive physical breakage of the beads. A solution consisting of 33.1g of silver sulfate and 5,000 ml of deionized water is added to the resin slurry at room temperature over a 6 minute period. The stirring is reduced to a slow rate and is continued for an additional 60 minutes. The composition is filtered (filtrate contains approximately 40 ppm silver) and washed twice with water to give 4,000 ml (2,416g) of product. The microbiocidal composition contains approximately 3.25–3.5% silver (as determined by elemental analysis).

EXAMPLE II

Preparation of AMBERLITE IRA-938($I_3^-$) Resin Microbiocidal Composition

A 1500 ml (898g) sample of AMBERLITE IRA-938(Cl) resin is converted to the iodide form by a column process using 8 liters of a 1N potassium iodide solution at a flow rate of two liters per hour. The resin is washed with deionized water to remove the excess potassium iodide.

To a five liter flash equipped with an overhead stirrer and thermometer is added 2,780 ml of deionized water and 461.7g of potassium iodide. The solution is heated to 80° C and 201.9g of iodine is added. The triiodide solution is cooled to room temperature and the above pretreated AMBERLITE IRA-938($I^-$) is added. The mixture is stirred for 4 hours at room temperature. The supernatent liquid is removed by filtration and the beads are washed with deionized water and transferred to a column. The beads are column washed with 8 liters of 1N potassium iodide followed by 8 liters of deionized water. The washing process is repeated and the microbiocidal composition is used in the bacteriological studies without any further purification.

EXAMPLE III

Preparation of AMBERLITE IRA-938 resin - Reduced Silver Microbiocidal Composition A 100 ml sample of AMBERLITE IRA-938(Cl) resin was converted to the dithionite form using 1 liter of 4% sodium dithionite solution. A 50 ml sample of this resin was treated with a solution consisting of 1.13g (6.6 meq.) of silver nitrate dissolved in 200 ml of water in a batchwise process with slow stirring. After a 1 hour reaction period the resin was filtered and conditioned by washing with 4% sodium nitrate, deionized water, 4% sodium chloride and deionized water.

EXAMPLE IV

Preparation of AMBERLITE ® 200 Resin - Reduced Silver Microbiocidal Composition

AMBERLITE ® 200 resin, (a strong acid small pore macroreticular styrene/divinyl benzene resin of Rohm and Haas Company) (600g. wet) was converted to the ionic silver form using 836 ml of 0.4N silver nitrate in a column process. The resin was washed with deionized water to remove excess silver nitrate. A 385 ml sample of this resin was placed in a 2-liter beaker and treated with 583 ml of 5% sodium dithionite. After stirring the mixture for 30 minutes, the resin was filtered and column washed with deionized water, 4% hydrochloric acid, and deionized water.

The large pore macroreticular anion exchange microbiocidal compositions of the present invention are superior to known gel and small pore macroreticular anion exchange resins at removing coliform bacteria from contaminated water. Table I below presents a comparison of the large pore macroreticular anion exchange resin, utilized in making the microbiocidal compositions of the present invention, with known anion exchange resins. All of these anion exchange resins are in the chloride form and were treated with inoculum containing *Escherichia coli* (1,460,000–1,740,000 cells/ml) and 200 ppm NaCl.

Table I

| AMBERLITE® Resins[a] | Average Critical Dimension Range A | Viable Cells/100 ml of processed inoculum | % Reduction[b] | Viable Cells/100 ml of processed inoculum | % Reduction[c] |
|---|---|---|---|---|---|
| IRA-938 | 25,000–250,000 | 15 | 99.9991 | 97 | 99.993 |
| XE-313 | ca. 12,000 | 345 | 99.98 | 2,000 | 99.9 |
| IRA-904 | 210 –1200 | 4,000 | 99.8 | 304,000 | 80.5 |
| IRA-400 | gel | 112,000 | 93.4 | 250,000 | 85.6 |
| IRA-910 | 70–300 | 180,000 | 89.4 | 468,000 | 73.1 |
| IRA-900 | 140–220 | 528,000 | 68.9 | 254,000 | 85.4 |
| IRA-410 | gel | 598,000 | 64.8 | 578,000 | 66.8 |

[a] A minimum amount of resin, (40 ml of resin in an 18 inch bed height column of 11 mm diameter), and high flow rates were utilized in the experiment.
[b] 40–60 mesh beads, 15 gpm/ft³ flow rate.
[c] 30–40 mesh beads, 20 gpm/ft³ flow rate.

The results of Table I show that the large pore (about 12,000A to about 250,000A) macroreticular anion exchange resins, utilized in preparing the microbiocidal compositions of the present invention, are superior to the other smaller pore and gel resins in permanently trapping the *Escherichia coli* from the inoculum. The small volume of resin and the high flow rates were utilized in the experiment to demonstrate the differences in bacteria removal ability. For that reason, no attempt was made to achieve 100% bacteria reduction in the experiment.

The main problem with utilizing these large pore macroreticular anion exchange resins to merely trap out bacteria from the aqueous stream, is the fact that once the bacteria are trapped on the resin they are not killed. Thus, the possibility of eventual breakthrough of bacteria during long term use could present a serious problem, especially since the bacteria tend to multiply on the resin.

Table II below, shows the effects of various microbiocidal compositions of the present invention and their ability to both trap and kill *Escherichia coli.*

Five samples of AMBERLITE IRA-938(Cl) resin containing approximately 1.5%, 5%, 10%, 25% and 100% of precipitated silver chloride (based on exchange sites) were evaluated for microbiocidal activity and silver release using inoculum containing *E. coli* (ca. 20,000 cells/100 ml) and 200 ppm NaCl at a 15 gpm/ft$^3$ flow rate (24 inch bed height × 11mm diameter; 4 hour test). The exposed beads were evaluated for living cells following the test (after standing 20 hours). The test results are shown in Table II below.

Table II

| AMBERLITE® IRA-938(Cl)-AgCl Microbiocidal Comparison[a] | Viable Cells 100 ml | Ag in Effluent ppb | Living Cells/g[b] of Exposed Resin |
|---|---|---|---|
| 1.5% | 0 | 28 | 13,200 |
| 5% | 0 | 24 | 2,520 |
| 10% | 0 | 27 | 252 |
| 25% | 1 | 24 | 54 |
| 100% | 4 | — | 10 |

[a]The microbiocidal compositions are identified by the % of the exchange sites of AMBERLITE IRA-938(Cl) resin reacted with 0.1N AgNO$_3$.
[b]Data is shown to indicate trend. Bactericidal evaluation of contaminated beads often gives uncertain results. Exposed AMBERLITE IRA-938 (Cl) with 0% AgCl is highly contaminated (too numerous to count).

The microbiocidal composition composed of AMBERLITE IRA-938(Cl) resin containing small quantities of silver chloride (1.5 - 10%) is as effective as AMBERLITE IRA-938(Cl) resin at removing *E. coli.* Increasing the silver chloride content apparently partially blocks some of the pores causing a slight decrease in bacteria reduction. The solubility of silver chloride is less than 50 ppb in water containing greater than 10 ppm chloride ion. Thus, the amount of silver released is kept below 50 ppb by the addition of the 200 ppm of sodium chloride. The results shown in Table II demonstrate that the silver chloride is effective in killing the bacteria that are absorbed on the microbiocidal composition. The data further indicates that a more rapid kill occurs with the microbiocidal compositions containing the higher percentages of silver chloride. However, even at 1.5% silver chloride content there is a reduction in the number of living cells per gram of exposed resin.

In order to test the physical stability of the large pore macroreticular anion exchange resins utilized in the present invention the following experiment was carried out.

A 1-liter sample of AMBERLITE IRA-938(Cl, 30-40 mesh) resin in a high pressure canister was connected to a water line for an under the sink attrition test. The water pressure varied from 65-70 PSI and occasionally would surge to 95 PSI. The flow rate was 3.5 gal/min. Table III shows the effect of on-off cycling on the flow rate and bead appearance. The on-off cycling rate was set at 20 cycles/min.

Table III

| No. Cycles | Flow Rate (gal/min) | Bead Appearance |
|---|---|---|
| 900 | 3.5 | OK |
| 7,200 | 3.5 | OK |
| 14,400 | 2.1 | Fines and whole beads |

A significant flow rate reduction occurred by 14,400 cycles at which point the flow rate had dropped from 3.5 to 2.1 gal/min. A noticeable but insignificant change in flow rate occurred near 11,000 cycles. Eleven thousand cycles represents about 4 months of under the sink use assuming that 100 on-off cycles/day is typical for an average household.

Table IV demonstrates the bactericidal evaluation of AMBERLITE IRA-938(Cl) resin using *Streptococcus faecalis* and *Pseudomonas aeruginosa.* Several short-term tests show that other bacteria, namely, *Streptococcus faecalis* and *Pseudomonas aeruginosa,* are also effectively adsorbed by AMBERLITE ERA-938(Cl) resin. *Streptococcus faecalis* and *E. coli* are non-pathogenic bacteria used as indicators of water purity, that is, their presence in a water supply is an indication of fecal contamination. *Pseudomonas aeruginosa* is a common pathogen which is particularly resistant to quaternary amine biocides and to many antibacterial drugs. Both *E. coli* and *Pseudomonas aeruginosa* are Gram-negative rods (ca. 0.5 mm - 2.0 mm). *Streptococcus faecalis* is a Gram-positive cocci, approximately 1 mm in diameter, and occurs in chains of varying lengths.

In a short-term comparative test, the chloride form of AMBERLITE IRA-938 (18 inch bed height × 11 mm diameter) effected excellent reduction of both *E. coli* and *Streptococcus faecalis* from highly concentrated inoculum (260,000 cells/ml and 167,000 cells/ml, respectively) containing 200 ppm sodium chloride (see Table IV).

Table IV

| Flow Rate (gpm/ft$^3$) | *E. Coli*[a] No. Cells/ ml Effluent | % Reduction | *S. faecalis*[b] No. Cells/ ml Effluent | % Reduction |
|---|---|---|---|---|
| 2 | 605 | 99.8 | 83 | 99.95 |
| 5 | 675 | 99.7 | 111 | 99.93 |
| 10 | 605 | 99.8 | 470 | 99.7 |

[a]*E. coli* inoculum = 260,000 cells/ml
[b]*S. faecalis* inoculum = 167,000 cells/ml Table IV demonstrates that an AMBERLITE IRA-938 (Cl) resin bed having a height of 22.5 inches and an 11 mm diameter gave complete *Pseudomonas aeruginosa* reduction from inoculum containing 32,000 cells/100 ml and 200 ppm NaCl at a 100 ml/minute flow rate (70 minute exposure time).

Table V gives the bactericidal evaluation of AMBERLITE IRA-938(I$_3$-) resin in conjunction with a novel scavenger system. Iodine, iodide release is a major problem associated with the use of triiodide resins for potable water applications. The AMBERLITE IRA-938(Cl) resin however, can function as a bacteria scavenger as well as an iodine scavenger, and the use of a reduced silver resin releases safe levels of silver to kill the adsorbed bacteria. The feasibility of the dual purpose scavenger concept is demonstrated in the following short-term column test.

The triiodide form of AMBERLITE IRA-938 (10 ml) and a reduced silver resin (10 ml), was treated with inoculum containing *E. coli* (1,880,000 cells/100 ml) and 200 ppm NaCl. The test results are shown in Table V below.

Table V

| Flow Rate (gpm/ft$^3$) | Microbiocidal Composition | Viable Cells/ 100 ml | % Kill | Total I$_2$, I$^-$(ppm) | Silver in Effluent (ppm) |
|---|---|---|---|---|---|
| 10 | IRA-938(I$_3$$^-$) | 1,288 | 99.93 | 26 | |
|  | Scavenger | 32 | 99.99 | .05 | 54 |
| 20 | IRA-938(I$_3$$^-$) | 20,000 | 98.94 | 13.5 | |
|  | Scavenger | 264 | 99.99 | 0 | 42 |

Table V-continued

| Flow Rate (gpm/ft³) | Microbiocidal Composition | Viable Cells/ 100 ml | % Kill | Total $I_2$, $I^-$ (ppm) | Silver in Effluent (ppm) |
|---|---|---|---|---|---|
| 40 | IRA-938($I_3^-$) | 37,000 | 98.0 | 8 | |
|  | Scavenger | 3,000 | 99.8 | .015 | 38 |
| 75 | IRA-938($I_3^-$) | 67,000 | 96.44 | 5.8 | |
|  | Scavenger | 1,000 | 99.95 | .03 | 40 |

The biocidal activity of AMBERLITE IRA-938($I_3^-$) appears to be greater than 99.9% kill at 10 gallons per minute per cubic foot flow rates as shown in the above small column, high flow rate experiments.

The scavenger system scavenged all forms of iodine and iodide (0–0.5 ppm leakage) and adsorbed bacteria (>90%) that survived the triiodide resin. Evaluation of the scavenger resin following the test showed 252 living cells/g of resin. Bacterial contamination on the scavenger resin without the silver present is normally too high to count.

As demonstrated above, the large pore macroreticular anion exchange microbiocidal compositions of the present invention and various combinations thereof are effective in entrapping and killing microbes commonly found in contaminated water. Furthermore, these compositions allow for their in line use at high flow rates. The microbiocidal compositions of the present invention can be utilized in various ways such as in the purification of drinking water and swimming pool water. They can also be utilized in other aqueous solutions such as physiological fluids and the like. The above uses of the compositions of the present invention as well as those other applications which readily present themselves to those skilled in the art of fluid processes are all within the breadth and scope of the present specification and claims.

I claim:

1. A microbiocidal composition which comprises a large pore macroreticular strong base anion exchange resin containing quaternary ammonium groups, wherein the average critical dimension of the macroreticular anion exchange pore is in the range of from about 8,000 A to about 500,000 A which contains a physically bound silver chloride microbiocide.

2. A method of purifying microbially contaminated water which comprises passing said contaminated water through a microbiocidal composition according to claim 1.

3. A method according to claim 2 wherein the microbes are gram-negative and gram-positive bacteria, viruses, fungi, lichens, algae slime and molds.

4. A method according to claim 2 wherein the microbes are gram-negative and gram-positive bacteria.

5. A method of purifying microbially contaminated aqueous solutions which comprises passing said contaminated aqueous solution through a microbiocidal composition according to claim 1.

6. A process for the preparation of the microbiocidal composition according to claim 1 which comprises:
   a. stirring an aqueous mixture of a preconditioned large pore macroreticular anion exchange resin in the chloride anion form;
   b. adding a water soluble silver salt to said mixture at about room temperature and contacting for a period of about an hour;
   c. filtering the resin and washing it with water.

7. A process according to claim 6 which includes the additional step of drying the washed resin at temperatures from about 40° C to about 110° C.

8. A process according to claim 6 wherein the water soluble silver salt is selected from the group consisting of silver sulfate, silver nitrate, silver acetate, silver carbonate, silver oxide and silver tartarate.

9. A process according to claim 8 wherein said water soluble silver salt is silver sulfate.

* * * * *